(12) United States Patent
Magnani et al.

(10) Patent No.: US 6,387,884 B1
(45) Date of Patent: *May 14, 2002

(54) LEUKOCYTE HOMING MODULATION

(75) Inventors: John L. Magnani, BioCarb Incorporated 300 Professional Dr., Suite 100, Gaithersburg, MD (US) 20879; Eugene C. Butcher, Portola Valley; Ellen L. Berg, Fremont, both of CA (US)

(73) Assignees: Stanford University, Palo Alto, CA (US); John L. Magnani, Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/336,417

(22) Filed: Nov. 9, 1994

Related U.S. Application Data

(63) Continuation of application No. 07/688,037, filed on Apr. 19, 1991, now abandoned, which is a continuation-in-part of application No. 07/614,616, filed on Nov. 16, 1990, now abandoned, which is a continuation-in-part of application No. 07/539,844, filed on Jun. 18, 1990, now abandoned.

(51) Int. Cl.$^7$ ...................... A61K 31/70; A61K 31/715
(52) U.S. Cl. .............................. 514/25; 514/8; 514/23; 514/53; 514/54; 514/61; 514/62; 530/395; 536/1.11; 536/4.1; 536/17.2; 536/18.7
(58) Field of Search .............................. 514/23, 53, 54, 514/61, 62, 8.25; 530/395; 536/1.11, 17.2, 4.1, 18.7

(56) References Cited

U.S. PATENT DOCUMENTS

| | | | |
|---|---|---|---|
| 4,471,057 A | 9/1984 | Koprowski et al. | 436/518 |
| 4,851,511 A | 7/1989 | Hakomori et al. | |
| 4,859,769 A | 8/1989 | Karlsson et al. | 536/53 |
| 4,876,199 A | 10/1989 | Hakomori | 530/387 |
| 5,143,712 A | * 9/1992 | Brandley et al. | 424/1.1 |
| 5,211,937 A | * 5/1993 | Brandley et al. | 424/1.1 |
| 5,538,724 A | 7/1996 | Butcher et al. | 424/152.1 |
| 5,723,583 A | * 3/1998 | Seed et al. | 530/387.3 |

FOREIGN PATENT DOCUMENTS

| | | |
|---|---|---|
| EP | 408 859 A2 | 1/1991 |
| WO | WO 90/13300 | 11/1990 |
| WO | WO 91/19502 | 12/1991 |
| WO | WO 92/01718 | 2/1992 |
| WO | WO 92/07572 | 5/1992 |

OTHER PUBLICATIONS

Edgington, Biotechnology, 10: 383–389, May 1992.*

Ward et al., Therapeutic Immunology, 1: 165–171, Jan. 1994.*

Baeckström et al., "Purification and Characterization of a Membrane–bound and a Secreted Mucin–type Glycoprotein Carrying the Carcinoma–associated Sialyl–Le$^a$ Epitope on Distinct Core Proteins," *J. Biol. Chem.* 266(32):21537–21547, 1991.

Berg et al., "The Cutaneous Lymphocyte Antigen Is a Skin Lymphocyte Homing Receptor for the Vascular Lectin Endothelial Cell–Leukocyte Adhesion Molecule 1," *J. Exp. Med.* 174:1461–1466, 1991.

Berg et al., "A Carbohydrate Domain Common to Both Sialyl Le$^a$ and Sialyl Le$^x$ Is Recognized by the Endothelial Cell Leukocyte Adhesion Molecule ELAM–1," *J. Biol. Chem.* 266(23): 14869–14872, 1991.

Bird and Kimber, "Oligosaccharides Containing Fucose Linked α(1–3) and α(1–4) to N–Acetylglucosamine Cause Decompaction of Mouse Morulae," *Devel. Biol.* 104:449–460, 1984.

Bowen et al., "Characterization of a Human Homologue of the Murine Peripheral Lymph Node Homing Receptor," *Journal of Cell Biology* 109:421–427, 1989.

Brandley et al., "Carbohydrate Ligands of LEC Cell Adhesion Molecules," *Cell* 63:861–863, 1990.

Broquet et al., "Effect of Desipramine on a Glycoprotein Sialyltransferase Activity in C6 Cultured Glioma Cells," *J. Neurochem.* 54:388–394, 1990.

Childs et al., "High–molecular–weight glycoproteins are the major carriers of the carbohydrate differentiation antigens I, i and SSEA–1 of mouse teratocarcinoma cells," *Biochem. J.* 215:491–503, 1983.

Ching and Rhodes, "Purification and Characterization of a Peanut–Agglutinin–Binding Pancreatic–Cancer–Related Serum Mucus Glycoprotein," *Int. J. Cancer* 45:1022–1027, 1990.

Corral et al., "Requirement for Sialic Acid on Neutrophils in a GMP–140 (PADGEM) Mediated Adhesive Interaction with Activated Platelets," *Biochem. Biophys. Res. Commun.* 172:1349–1356, 1990.

(List continued on next page.)

*Primary Examiner*—Kathleen K. Fonda
(74) *Attorney, Agent, or Firm*—Seed Intellectual Property Law Group PLLC

(57) ABSTRACT

Novel methods and compositions are provided for modulating homing of leukocytes, particularly lymphocytes, where the compounds are cross-reactive with Neu5Ac2-3Galβ1–X[Fucα1–y]GlcNAc, where one of x and y is three and the other is four. These compounds may be administered to a host associated with inflammation, to avoid the deleterious effects of leukocyte infiltration.

3 Claims, 1 Drawing Sheet

OTHER PUBLICATIONS

Duijvestijn et al., "High Endothelial Differentiation in Human Lymphoid and Inflammatory Tissues Defined by Monoclonal Antibody HECA–452," *Am. J. Path.* 130:147–155, 1988.

Eggens et al., "A Role of Carbohydrate–Carbohydrate Interaction in the Process of Specific Cell Recognition During Embryogenesis and Organogenesis: A Preliminary Note," *Biochem. Biophys. Res. Commun.* 158(3):913–920, 1989.

Eggens et al., "Specific Interaction between $Le^x$ and $Le^x$ Determinants. A Possible Basis for Cell Recognition in Preimplantation Embryos and in Embryonal Carcinoma Cells," *J. Biol. Chem.* 264(16):9476–9484, 1989.

Fenderson et al., "The blood group I antigen defined by monolconal antibody C6 is a marker of early mesoderm during murine embryogenesis," *Differentiation* 38:124–133, 1988.

Fenderson et al., "A Multivalent Lacto–N–Fucopenatose III–Lysyllysine Conjugate Decompacts Preimplantation Mouse Embryos, While the Free Oligosaccharide is Ineffective," *J. Exp. Med.* 106:1591–1596, 1984.

Fenderson et al., "Coordinate Expression of X and Y Haptens during Murine Embryogenesis," *Devel. Biol.* 114:12–21, 1986.

Fukushi et al., "Novel Fucolipids Accumulating in Human Adenocarcinoma. II. Selective Isolation of Hybridoma Antibodies That Differentially Recognize Mono–, Di–, and Trifucosylated Type 2 Chain," *J. Biol. Chem.* 259(7):4681–4685, 1984.

Fukushi et al., "Novel Fucolipids Accumulating in Human Adenocarcinoma. III. A Hybridoma Antibody (FH6) Defining a Human Cancer–Associated Difucoganglioside $(VI^3NeuAcV^3Fuc_2nLc_6)$," *J. Biol. Chem.* 259(16):10511–10517, 1984.

Gabius et al., "Endogenous Tumor Lectins: Overview and Perspective," *Anticancer Res.* 6:573–578, 1986.

Gallatin et al., "A cell–surface molecule involved in organ–specific homing of lymphocytes," *Nature* 304:30–34, 1983.

Gooi et al., "Stage–specific embryonic antigen involves α 1 → 3 fucosylated type 2 blood group chains," *Nature* 292:156–158, 1981.

Hakamori et al., "Novel Fucolipids Accumulating in Human Adenocarcinoma. I. Glycolipids With Di– or Trifucosylated Type 2 Chain," *J. Biol. Chem.* 259(7):4672–4680, 1984.

Hakomori et al., "The Hapten Structure of a Developmentally Regulated Glycolipid Antigen (SSEA–1) Isolated From Human Erythrocytes and Adenocarcinoma: A Preliminary Note," *Biochem. Biophys. Res. Comm.* 100(4):1578–1586, 1981.

Hakomori S., "Aberrant Glycosylation in Cancer Cell Membrane as Focused on Glycolipids: Overview and Perspectives," *Cancer Res.* 45:2405–2414, 1985.

Handa et al., "Selectin GMP–140 (CD62; PADGEM) Binds to Sialosyl–$Le^a$ and Sialosyl–$Le^x$, and Sulfated Glycans Modulate this Binding," *Biochemical and Biophysical Research Communications* 181(3):1223–1230, 1991.

Hansson and Zopf, "Biosynthesis of the Cancer–associated Sialyl–$Le^a$ Antigen," *Journal of Biological Chemistry* 260(16):9388–9392, 1985.

Holmes et al., "Enzymatic Basis for the Accumulation of Glycolipids with X and Dimeric X Determinants in Human Lung Cancer Cells (NCI–H69)," *J. Biol. Chem.* 260(12):7619–7627, 1985.

Huse et al., "Generation of a Large Combinatorial Library of the Immunoglobulin Repertoire in Phage Lambda," *Science* 246:1275–1281, 1989.

Hynes, R., "Integrins: A Family of Cell Surface Receptors," *Cell* 48:549–554, 1987.

Issekutz, T., "Inhibition of in Vivo Lymphocyte Migration of Inflammation and Homing to Lymphoid Tissues by the TA–2 Monoclonal Antibody. A Likely Role for VLA–4 in Vivo," *Journal of Immunology* 147:4178–4184, 1991.

Jeffrey et al., "Affinity Chromatography of Carbohydrate–Specific Immunoglobulins: Coupling of Oligosaccharides to Sepharose," *Biochem. Biophys. Res. Commun.* 62:608–613, 1975.

Kannagi et al., "New Globoseries Glycosphingolipids in Human Teratocarcinoma Reactive with the Monoclonal Antibody Directed to a Developmentally Regulated Antigen, Stage–specific Embryonic Antigen 3," *J. Biol. Chem.* 258(14):8934–8942, 1983.

Kannagi et al., "Stage–specific embryonic antigens (SSEA–3 and –4) are epitopes of a unique globo–series ganglioside isolated from human teratocarcinoma cells," *Embo J.* 2(12):2355–2361, 1983.

Karaivanova et al., "Partial Characterization of Microsomal Sialyltransferase From Chicken Liver and Hepatoma Mc–29: II. Measurements of Enzyme Activities Utilizing Microsomal Glycoproteins as Exogenous Acceptors," *Cancer Biochem. Biophys.* 11:311–315, 1990.

Kitagawa et al., "Immunoaffinity Isolation of Sialyl–$Le^a$ Oligosaccharide from Human Milk," *J. Biochem.* 104:591–594, 1988.

Kitagawa et al., "Characterization of Mucin–Type Oligosaccharides With the Sialyl–$Le^a$ Structure From Human Colorectal Adenocarcinoma Cells," *Biochem. Biophys. Res. Commun.* 178(3):1429–1436, 1991.

Köhler and Milstein, "Continuous cultures of fused cells secreting antibody of predefined specificity," *Nature* 256:495–497, 1975.

Köhler and Milstein, "Derivation of specific antibody–producing tissue culture and tumor lines by cell fusion," *Eur. J. Immunol.* 6:511–519, 1976.

Kojima and Hakomori, "Specific Interaction between Gangliotriaosylceramide $(G_{g3})$ and Sialosyllactosylceramide $(G_{M3})$ as a Basis for Specific Cellular Recognition between Lymphoma and Melanoma Cells," *J. Biol. Chem.* 264(34):20159–21062, 1989.

Koprowski et al., "Colorectal Carcinoma Antigens Detected by Hybridoma Antibodies," *Somatic Cell Genetics* 5(6):957–972, 1979.

Kuzuoka, "Antitumor activity of murine monoclonal antibody NCC–ST–421," *Chem. Ab.* 115:27344v, 1991.

Lamblin et al., "Primary Structure Determination of Five Sialylated Oligosaccharides Derived from Bronchial Mucus Glycoproteins of Patients Suffering from Cystic Fibrosis. The Occurrence of the NeuAcα(2→3)Galβ(1→)[Fucα(1→3)]GlcNAcβ(1→•) Structural Element Revealed By 500–MHz H NMR Spectroscopy," *Journal of Biological Chemistry* 259(14):9051–9058, 1984.

Larsen et al., PADGEM–Dependent Adhesion of Platelets to Monocytes and Neutrophils Is Mediated by a Lineage–Specific Carbohydrate, LNF III (CD15), *Cell* 63:467–474, 1990.

Lindenberg et al., "Carbohydrate binding properties of mouse embyros," *J. Reprod. Fert.* 89:431–439, 1990.

Lipartiti et al., "Monosialoganglioside GM1 Reduces NDMA Neurotoxicity in Neonatal Rat Brain," *Experimental Neurology* 113:301–305, 1991.

Lowe et al., "A transfected human fucosyltransferase cDNA determines biosynthesis of oligosaccharide ligand(s) for endothelial–leukocyte adhesion molecule I," *Biochem. Soc. Trans.* 19(3):649–653, 1991.

Lowe et al., "ELAM–1–Dependent Cell Ahdesion to Vascular Endothelium Determined by a Transfected Human Fucosyltransferase cDNA," *Cell* 63:475–484, 1990.

Macher et al., "A Novel Carbohydrate, Differentiation Antigen of Fucogangliosides of Human Myeloid Cells Recognized by Monoclonal Antibody VIM–2," *Journal of Biological Chemistry* 263(21):10186–10191, 1988.

Magnani et al., "A Monoclonal Antibody–defined Antigen Associated with Gastrointestinal Cancer Is a Ganglioside Containing Sialylated Lacto–N–fucopentaose II," *Journal of Biological Chemistry* 257(23):14365–14369, 1982.

Magnani et al., "Identification of the Gastrointestinal and Pancreatic Cancer–associated Antigen Detected by Monoclonal Antibody 19–9 in the Sera of Patients as a Mucin," *Cancer Res.* 43:5489–5492, 1983.

Magnani, J., "Carbohydrate Sequences Detected By Murine Monoclonal Antibodies," *Chemistry and Physics of Lipids* 42:65–74, 1986.

Mulligan and Berg, "Selection for animal cells that express the *Escherichia coli* gene coding for xanthine–guanine phosphoribosyltransferase," *Proc. Natl. Acad. Sci. USA* 78:2072–2076, 1981.

Nicolaou et al., "Total Synthesis of the Tumor–Associated $Le^X$ Family of Glycosphinglolipids," *J. Amer. Chem. Soc.* 112:3693–3695, 1990.

Nudelman et al., "Novel Fucolipids of Human Adenocarcinoma: Disialosyl $Le^a$ Antigen ($III^4FucIII^6NeuAcIV^3NeuAcLc_4$) of human Colonic Adenocarcinoma and the Monoclonal Antibody (FH7) Defining This Structure," *J. Biol. Chem.* 261:5487–5495, 1986.

Palcic et al., "A Bisubstrate Analog Inhibitor for $\alpha(1\rightarrow 2)$–Fucosyltransferase," *J. Biol. Chem.* 264:17174–17181, 1989.

Palcic et al., "Enzymic Synthesis of Oligosaccharides Terminating in the Tumor–Associated Sialyl–Lewis–a Determinant," *Carbohydr. Res.* 190:1–11, 1989.

Palcic et al., "Regulation of N–Acetylglucosaminyltransferase V Activity. Kinetic Comparisons of Parental, Rous Sarcoma Virus–Transformed BHK, and L–Phytohemagglutinin–Resistant BHK Cells Using Synthetic Substrates and an Inhibitory Substrate Analog," *J. Biol. Chem.* 265:6759–6769, 1990.

Phillips et al., "ELAM–1 Mediates Cell Adhesion by Recognition of a Carbohydrate Ligand, Sialyl–$Le^x$," *Science* 250:1130–1132, 1990.

Picker et al., "The Neutrophil Selectin LECAM–1 Presents Carbohydrate Ligands to the Vascular Selectins ELAM–1 and GMP–140," *Cell* 66:921–933, 1991.

Prokazova et al., "Sialylated lactosylceramides. Possible inducers of non–specific immunosuppression and atherosclerotic lesions," *European Journal of Biochemistry* 172:1–6, 1988.

Rauvala et al., "Studies on Cell Adhesion and Recognition. I. Extent and Specificity of Cell Adhesion Triggered by Carbohydrate–reactive Proteins (Glycosidases and Lectins) and by Fibronectin," *J. Cell Biol.* 88:127–137, 1981.

Rice and Bevilacqua, "An Inducible Endothelial Cell Surface Glycoprotein Mediates Melanoma Adhesion," *Science* 246:1303–1306, 1989.

Ruoslahti and Pierschbacher, "New Perspectives in Cell Adhesion: RGD and Integrins," *Science* 238:491–497, 1987.

Sakurai et al., "Selection of a Monoclonal Antibody Reactive with a High–Molecular–Weight Glycoprotein Circulating in the Body Fluid of Gastrointestinal Cancer Patients," *Cancer Research* 48:4503–4058, 1988.

Sastry et al., "Cloning of the immunological repertoire in *Escherichia coli* for generation of monoclonal catalytic antibodies: Construction of a heavy chain variable region–specific cDNA library," *Proc. Natl. Acad. Sci. USA* 86:5728–5732, 1989.

Shitara et al., "Application of Anti–Sialyl $Le^a$ Monoclonal antibody, KM231, for Immunotherapy of Cancer," *Anticancer Res.* 11:2003–2014, 1991.

Stanley and Atkinson, "The LEC11 Chinese Hamster Ovary Mutant Synthesizes N–Linked Carbohydrates Containing Sialylated, Fucosylated Lactosamine Units. Analysis By One–and Two–Dimensional H NMR Spectroscopy," *J. Biol. Chem.* 263(23):11374–11381, 1988.

Stephens and Cockett, "The construction of highly efficient and versatile set of mammalian expression vectors," *Nucleic Acids Research.* 17:7110, 1989.

Streeter et al., "Immunohistologic and Functional Characterization of a Vascular Addressin Involved in Lymphocyte Homing into Peripheral Lymph Nodes," *Journal of Cell Biology* 107:1853–1862, 1988.

Stroud et al., "Extended Type 1 Chain Glycosphingolipids: Dimeric $Le^a$ ($III^4V^4Fuc_2Lc_6$) as Human Tumor–associated Antigen," *J. Biol. Chem.* 266(13):8439–8446, 1991.

Svenson and Lindberg, "Coupling of Acid Labile Salmonella Specific Oligosaccharides to Macromolecular Carriers," *J. Immunol. Meth.* 25:323–335, 1979.

Takada et al., "Adhesion of Human Cancer Cells to Vascular Endothelium Mediated by a Carbohydrate Antigen, Sialyl Lewis $A^1$," *Biochem. Biophys. Res. Commun.* 179(2):713–719, 1991.

Takeichi, M., "Cadherins: a molecular family essential for selective cell–cell adhesion and animal morphogenesis," *Trends Genet.* 3(8):213–217, 1987.

Trouet et al., "A covalent linkage between daunorubicin and proteins that is stable in serum and reversible by lysosomal hydrolases, as required for a lysosomotropic drug–carrier conjugate: In vitro and in vivo studies," *Proc. Natl. Acad. Sci. USA* 79:626–629, 1982.

Tyrrell et al., "Structural requirements for the carbohydrate ligand of E–selectin," *Proc. Natl. Acad. Sci. USA* 88:10372–10376, 1991.

Walz et al., "Recognition by ELAM–1 of the Sialyl–$Le^x$ Determinant on Myeloid and Tumor Cells," *Science* 250:1132–1135, 1990.

Whisler and Yates, "Regulation of Lymphocyte Responses By Human Gangliosides. I. Characteristics of Inhibitory Effects and the Induction of Impaired Activation," *Journal of Immunology* 125(5):2106–2111, 1980.

Zhou et al., "The Selectin GMP–140 Binds to Sialylated, Fucosylated Lactosaminoglycans on Both Myeloids and Nonmyeloid Cells," *Journal of Cell Biology* 115(2):557–564, 1991.

Zopf et al., "Affinity Purification of Antibodies Using Oligosaccharide–Phenethylamine Derivatives Coupled to Sepharose," *Meth. Enzymol.* 50:171–175, 1978.

\* cited by examiner

Sialyl Le^a Hexasaccharide

Sialyl Le^x Hexasaccharide

LEUKOCYTE HOMING MODULATION

CROSS-REFERENCE TO RELATED APPLICATIONS

This application is a continuation of U.S. patent application Ser. No. 07/688,037, filed Apr. 19, 1991, abandoned; which is a continuation in part of Ser. No. 07/614,616, filed Nov. 16, 1990, abandoned; which is a continuation in part of Ser. No. 07/539,844, filed Jun. 18, 1990, abandoned, all of which are incorporated herein by reference.

ACKNOWLEDGEMENTS

The inventions claimed in this application may have been supported in part by grants from the NIH. The U.S. Government may have an interest in this application.

INTRODUCTION

1. Technical Field

The field of this invention is the modulation of lymphocyte homing to provide therapies for inflammation and other pathogenic conditions associated with lymphocyte infiltration into tissue.

2. Background

The bloodstream is the pathway for numerous cells which migrate throughout the body, monitoring conditions. Cells of the lymphoid and myelomonocytic lineages act to identify foreign substances, such as pathogens, aberrant cells, and some compounds, and remove them from the system. These cells have available a large variety of mechanisms for protecting the host from the foreign substance. Many of these mechanisms are highly destructive and result in cytotoxicity of native tissue, inflammation, degradation, and the like. Mechanisms may involve the production of superoxide, secretion of various degradative compounds, such as perforans, endocytosis, etc.

While in many situations these protective mechanisms are salutary, in many other situations, they are found to have detrimental effects, involving inflammatory lesions, such as myocarditis, inflammatory bowel disease, psoriasis, allergic contact dermatitis, lichen planus, lymphoid hyperplasia in the skin, inflamed synovia, etc. There is, therefore, an interest in being able to modulate the effects of these various monitoring cells.

In recent years, it has been shown that the migrating cells have specific surface membrane proteins associated with their homing or being directed to a particular site. High endothelial venules serve as beacons for these cells, expressing proteins referred to as addressing, which bind to the "homing receptor" surface membrane proteins of the migrating cells. After binding to the high endothelial venules, the cells migrate by diapedesis, by mechanisms unknown, to the site of inflammation or injury. Therefore, by interfering with the binding between the addressin and the homing receptor, one may hope to reduce the infiltration of migrating cells into the inflamed site to prevent further aggravation of the site.

Relevant Literature

References associated with the characteristics of HECA-452 include Picker et al., *J. Immunol.* (1990) 145:3247–3255; Raine et al., *Clin. Immunol. Immunopathol.* (1990) 57:173–187; Jalkanen et al., *J. Invest. Dermatol.* (1990) 94:786–792; Picker et al., *Am. J. Pathol.* (1990) 136:1053–1068; VanDinther-Janssen et al., *J. Rheumatol.* 17:11–17; Jalkanen et al., *Int. J. Cancer* (1989) 44:777–782; Facchetti et al., *Immunol. Lett.* (1989) 20:277–281; Seldenrijk et al., *Gut* (1989) 30:46–491; Kabl et al., *J. Clin. Endocrinol. Metab.* (1989) 62:744–751; van der Valk et al., *Am. J. Surg. Pathol.* (1989) 13:97–106; Duijvestijn et al., *Am. J. Pathol.* (1988) 130:147–155; and Graber et al., *J. Immunol.* (1990) 145:819–830.

Lowe et al., *Cell* (1990) 63:475–484; Phillips et al., *Science* (1990) 250:1130–1132; Walz et al., *Science* (1990) 250:1132–1135; and Goelz et al., *Cell* (1990) 63:1349–1356, report a neutrophil carbohydrate ligand for ELAM-1 as NeUAcα2,3-galβ1-4 [Fucα1,3]GlcNac, the sialylated-Lewis X antigen, or sialylated lacto-N-fucopentaose III (sLNFIII).

SUMMARY OF THE INVENTION

Figure 1:
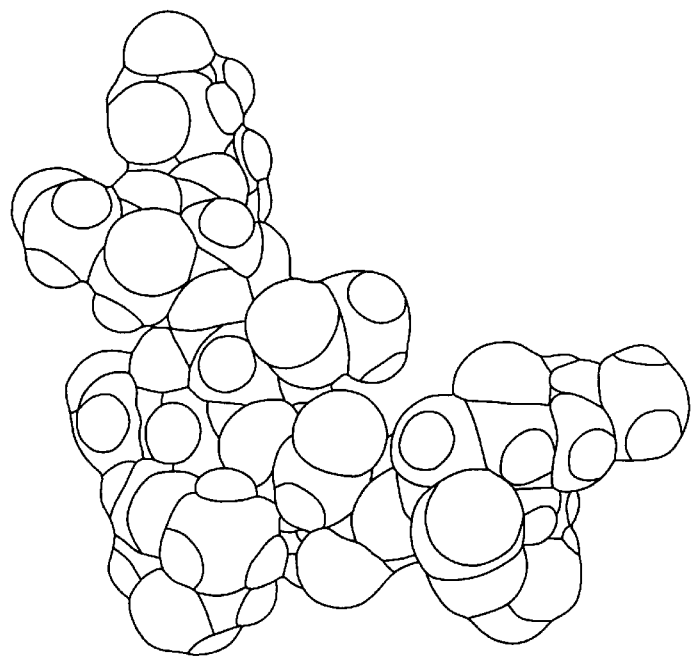
FIG. 1 is a graphic depiction of models for sialyl-Le$^a$ and sialyl-Le$^x$.
Figure 1:
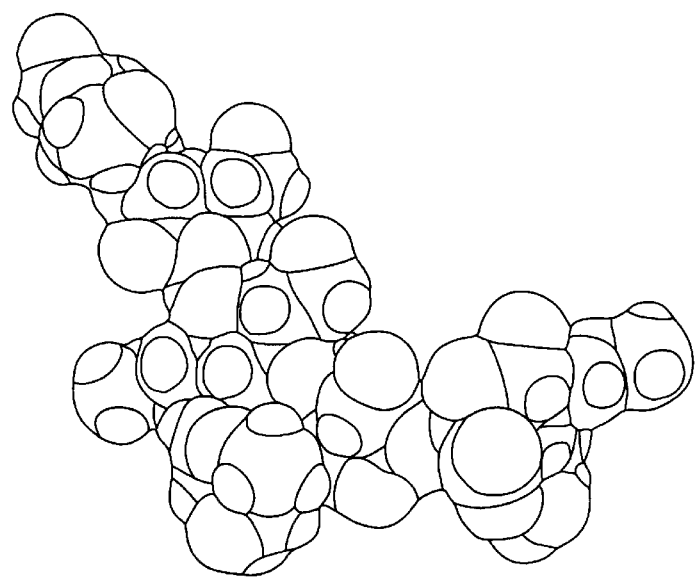

Compositions are provided for modulating the binding of leukocytes to addressins. The compositions are characterized by binding to the addressin ELAM-1, and are at least in part other than polypeptide and substantially free of the natural polypeptide associated with the homing receptor, the cutaneous lymphocyte associated antigen. These compositions find particular use in inhibiting the homing of leukocytes, particularly lymphocytes, to sites of inflammation.

DESCRIPTION OF THE SPECIFIC EMBODIMENTS

Novel methods and compositions are provided for the prophylactic and therapeutic modulation of homing of leukocytes, particularly lymphocytes, to sites of inflammation. The compositions are characterized by binding to ELAM-1, are cross-reactive with at least one epitope of sialyl-Le$^x$, and sialyl-Le$^a$, are other than sialyl-Le$^x$ and will usually involve at least about three saccharide monomer units.

The active structures of the compositions which find use will be under about 5,000 molecular weight and may be under about 3,000 molecular weight, generally being at least about 800 molecular weight. The compositions themselves may have multiple copies of the active structures, bonded to a common backbone (polymeric chain), liposomes, and the like. Any compound which has the above indicated characteristics of cross reactivity in binding to ELAM-1, is other than sialyl-Le$^x$ or protein conjugate thereof and is physiologically and pharmacokinetically acceptable may be employed. The compounds may be naturally occurring or synthetic and may be polysaccharides, synthetic organic compounds or the like.

Of particular interest are the sugars sialic acid (neuraminic acid), galactose, fucose, or derivatives thereof, combined to form an oligosaccharide derivative. The sugar monomers may be further derivatized by having up to four, usually not more than three groups bound to carbon, nitrogen or oxygen, which groups may include an additional sugar, such as sialic acid, glucosamine, galactose, glucose, fucose, etc. alkyl groups, such as methyl, ethyl, acyl groups, such as acetyl, etc. and the like. The site of substitution will not interfere with the binding of the compound to ELAM-1, but may provide such advantages as improved pharmacokinetics, stability, ease of synthesis, reduced toxicity, enhanced affinity, and the like.

Leukocytes which may be modulated as to their homing to cells expressing ELAM-1 include neutrophils, T-lymphocytes expressing the cutaneous lymphocyte-associated antigen, etc. These cells are found to home to a variety of injured, diseased, or otherwise patho-genic states, particularly associated with inflammation. Infiltration of these cells can be associated with such conditions as psoriasis, allergic contact dermatitis, lichen planus, lymphoid hyperplasia in the skin, non-specific chronic dermatitis, pityriasis lichenoids et varioformis acuta, granuloma annular, cutaneous drug eruption, pityriasis rubra pilaris, inflamed synovia, or the like.

The subject compositions may be prepared in accordance with conventional ways or isolated from a natural source, e.g. milk. Descriptions of the prepariations of sialyl-Le$^x$, sialyl-Le$^a$, the common portions of the two compounds, namely Neu5Ac2,3Galβ1-x[Fucα1-y] GlcNAc, wherein one of x and y is three, and the other is four, and cross-reactive derivatives thereof are illustrated by the synthesis of a variety of sugars which may be found in Paulsen, (1982) Angew. Chem. Int. Ed 94:184; Fugedi et al., (1987) Glycoconjugate J. 4:97 and Okamoto and Goto, (1990) Tetrahedron 46:5835 Kameyama et al. (1991) Carb. Res. 209:C1.

The compounds of this invention will be other than the naturally occurring Sialyl-Le$^a$ or Sialyl-Le$^x$ antigens found as polysaccharide markers on human cells. The compounds are characterized by having a structure which comprises or is immunologically cross-reactive with a structure that comprises a fucopyranose and a sialic acid or derivative thereof in a spatial conformation associated with both sialyl-Le$^a$ and sialyl-Le$^x$. Thus, the two sugars, sialic acid and fucopyranose will be bonded to a chain which permits the sugars to assume the proper orientation and spatial conformation, preferably provides restraint in maintaining such conformation. The backbone chain may be from 20 to 10, usually 3 to 8, preferably 3 to 7, more preferably 5 to 6 atoms, which may be carbon, nitrogen or oxygen, and may involve alicyclic, cyclic, heterocyclic or aromatic units or combinations thereof. Where a sugar is at least a portion of the backbone, desirably the sialic acid group will be present as the non-reducing terminal sugar of a disaccharide, where the other sugar is preferably galactose, and the disaccharide is separated by from about 1 to 4, preferably 1 to 3, particularly 2 atoms, usually carbon and optionally oxygen atoms, from the fucopyranose. The group serving as the separating chain desirably will be conformationally constrained, particularly as a cyclic or heterocyclic group. The group may be substituted with one or more oxy groups.

By conformationally constrained for cyclic groups are intended ranges of from 3 to 7, usually 5 to 6 annular members, or sterically hindered compounds, or other structures where the atoms of the chain are inhibited from free rotation.

The sialyl and fucopyranose groups may be cis or trans, equatorial or polar, in their spatial positions, usually trans.

For the most part, the subject compositions have as their core structure:

Neu5Acα2-3Galβ1-x[Fucα1-y]R wherein R is glucose or derivative thereof, e.g., glucosamine, N-acetyl glucosamine, etc., where any of the positions of the core structure may be substituted without interfering with the binding to ELAM-1. Sites for substitution include the available positions of galactose, glucose, and fucose, particularly with a sugar e.g. sialic acid, glucosamine, N-acetyl glucosamine, glucose, neuraminic acid, fucose, disaccharides thereof, etc., where the nitrogen atoms may be alkylated or acylated; and the like.

Of particular interest are compounds comprising a cyclic group to which fucose and a disaccharide with neuraminic acid as the non-reducing terminal sugar is bonded, where the fucose and disaccharide are separated by from 2 to 3 atoms, particularly carbon atoms and optimally an oxygen atom. Thus the cyclic compound may be of 5 to 7 annular members, particularly 6 annular members, and may include 1,2-cyclohexanediol, 1,3-cyclohexanediamine, 1,2-cyclohexanolamine, 1,2-cyclopentandiol, 2,3- or 3,4-dihydroxypyran, and the like. The positions may be cis or trans, preferably trans.

For a variety of purposes, the saccharidic compounds may be conjugated to other compounds, such as lipids, detergents, e.g. non-ionic detergents, such as polyalkyleneoxy groups, with alkylene of from 2–3 carbon atoms, usually under about 5 kDal, naturally occurring or synthetic organic compounds where the active structure is under about 2 kDal, which may be alicyclic, aromatic, acyclic or heterocyclic, polymeric compounds, such as physiologically acceptable polymers, e.g. acrylates, proteins, or the like, which may be under about 100 kD or more.

Proteins which may find use as carriers include serum albumin, casein, gelatin, etc. Conjugates may be prepared as immunogens to produce antisera or monoclonal antibodies specific for the binding epitope. Thus, antibodies could be used to inhibit homing of lymphocytes. Anti-idiotypic antibodies may be prepared which would compete with the binding epitope for the addressin to prevent lymphocyte infiltration.

The subject compounds may be conjugated to the carriers directly, but more usually through a spacer. Various spacers are known for linking to proteins, particularly spacers incorporating aromatic groups, e.g., phenylene, substituted with from 1 to 2 amino groups where the other functionality may be a carboxylic acid, aldehyde, mercaptan, activated olefin or the like. In bonding the spacer to the saccharide through an amino group, the linkage may provide for retention of the anomeric configuration of the reducing sugars or reductive amination may be employed resulting in an aminoalditol. (Kallin et al. (1986) Glycoconjugate J. 3:311).

Based on the configuration of the binding epitope, using computer assisted design, synthetic organic compounds can be devised which would compete with the binding epitope for the addressin.

The subject compositions may be administered in any convenient way, depending upon the particular nature of the composition. Various physiologically acceptable media may be employed, such as deionized water, saline, phosphate buffered saline, aqueous ethanol, and the like. Depending upon the nature of the compound, it may be administered typically, parenterally or orally, subcutaneously, intravascularly, topically, peritoneally, and the like. The particular dosage will vary with the frequency of administration, the manner of administration, the activity of the compound, the indication being treated, and the like.

The following examples are offered by way of illustration and not by way of limitation.

EXPERIMENTAL

Materials and Methods

Synthetic Glycoproteins (Neoglycoproteins)

The neoglycoproteins used in this paper were produced in BioCarb AB (Lund, Sweden) by chemically coupling 10–20 moles of a specific oligosaccharide to 1 mole of nonglycosylated albumin (bovine or human). The resulting synthetic glycoprotein (neoglycoprotein) contains multiple copies of the identical carbohydrate sequence, thereby producing a well characterized, mutivalent glycoconjugate which is extremely effective for studying carbohydrate-protein interactions. Depending on the size of the oligosaccharide, three different chemical spacer arms were used to couple the oligosaccharides to proteins 1) p-aminophenyl (PAP); 2) aminophenylethyl (APE); and 3) acetyl phenylene diamine were used to couple the shorter oligosaccharides to albumin since they will retain the anomeric configuration of the reducing sugars which may be involved in a potential binding site. APD was used to couple the larger sugars to protein by reductive amination, which converts the reducing sugar to an aminoalditol. These reduced sugars are designated by parenthesis in the APD conjugates presented in Table I.

TABLE 1

| NAME | STRUCTURE |
|---|---|
| LNF I (H-type 2) | Fucα1-2Galβ1-3GlcNAcβ1-3Galβ1-4(Glc) |
| LNF II ($Le^a$) | Galβ1-3GlcNAcβ1-4(Glc)<br>\|4<br>Fucα1 |
| LNF III ($Le^x$) | Galβ1-4GlcNAcβ1-3Galβ1-4(Glc)<br>\|3<br>Fucα1 |
| sLNFII ($sLe^a$) | Neu5Acα2-3Galβ1-3GlcNAcβ1-3Galβ1-4(Glc)<br>\|4<br>Fucα1 |
| sLNFIII ($sLe^x$) | Neu5Acα2-3Galβ1-4GlcNAcβ1-3Galβ1-4(Glc)<br>\|3<br>Fucα1 |
| LSTa | Neu5Acα2-3Galβ1-3GlcNAcβ1-3Galβ1-4(Glc) |
| LSTc | Neu5Acα2-6Galβ1-4GlcNAcβ1-3Galβ1-4(Glc) |
| 3' Sialyllactose | NeuNAc α2-3Gal β1-4 (Glc) |
| 6' Sialyllactose | NeuNAc α2-6Gal β1-4 (Glc) |

Monoclonal Antibodies

The monoclonal antibodies employed in these studies include the following. HECA-452, a rat IgM [anti-CLA, (Picker et al. (1990) *J. Immunol.* 145:3247–3255)] (Duijvestijn et al (1988) *Am. J. Path* 30:147–155; MECA-79, rat IgM control [anti-peripheral lymph node addressin (Streeter et al. (1988) *J. Cell Biol.* 107:1853–1862)]; RB6-2C2, rat IgM control [Coffman and Weissman (1981) *J. Exp. Med.* 153:269]; CL2 (anti-ELAM-1) (Picker et al. (1991), *Nature* 349:796–799), mouse $IgG_1$, kindly supplied by C. Wayne Smith (Houston, Tex.); Dreg-56, mouse $IgG_1$ [anti-human LECAM-1, (Kishimoto et al. (1990) *Proc. Nat'l Acad. Sci. USA* 87:2244–2248)]; CSLEXI (TT-19, anti-sLNFIII) (Fukushima et al. (1984) *Cancer Res.* 44:5279–5286), a mouse IqM, kindly given by P. Terasaki (UCLA); and 1H10 (anti-Sialyl $Le^a$) a mouse $IgG_1$ developed by BioCarb.

Direct Binding of Antibodies to Synthetic Glycoproteins (Neoglycoproteins)

Synthetic glycoproteins were coated onto microtiter plates by filling each well with 100 ng of the neoglycoprotein in 100 μl of 0.15 M sodium chloride, 0.01 M sodium phosphate, 0.1% sodium azide, pH 7.4, (PBS-azide) overnight at 4° C. Standard enzyme-linked immunoassays (ELISA) were then performed on the solid phase carbohydrate structures using the appropriate antibody diluted to 10 μg/ml.

Production of ELAM-1 cDNA Transfected Cell Lines

L1-2/pMRB107 cells (L1-$2^{ELAM-1}$) were prepared by transfecting the ELAM-1 gene into the murine pre-B cell line L1-2 (Gallatin et al. (1983) *Nature* 304:30–34). A cDNA clone encoding ELAM-1 was obtained from a cDNA library made from activated human umbilical vein endothelial cell cultures by polymerase chain reaction amplification. The ELAN-1 gene was inserted downstream of the hCMV promoter in pMRB101 [a derivative of EE6 which contains the *E. coli* gpt gene (Mulligan and Berg (1981) *Proc. Nat'l. Acad. Sci. USA* 78:2072; Stephens and Corbett (1989) *N.A.R.* 17:7110)]. DNA was introduced into L1-2 cells by electroporation and the cells selected for resistance to mycophenolic acid. A population of cells staining brightly for ELAM-1 were selected by FACS and cloned by limiting dilution. These cells are ELAM-$1^{hi}$ LFA-$1^{mod}$ CD$45^{hi}$ CD$44^{neg}$ LECAM-$1^{neg}$, differing from the parent cell line or control vector transfectants only in their expression of ELAM-1. L1-2/pMRB101 (L1-$2^{vector}$) cells are a similarly transformed derivative of L1-2 transfected with pMRB101 and lacking ELAM-1 expression.

Cell Binding Assays

One hundred microliter samples of each synthetic glycoconjugate in phosphate buffered saline (PBS), pH 7.2, were absorbed onto glass wells of 8-chamber slides (LabTek) for two hours at RT. For some experiments glass slides were pre-coated with rabbit anti-human serum albumin (Sigma) at 200 μg/ml overnight at 4° C. and washed with PBS prior to the addition of the glycoconjugate. After blocking with 5% NBS/10 mM HEPES/Dulbecco's Modified Eagles Medium (DMEM), pH 7.0 (CM), L1-$2^{ELAM-1}$ or L1-$2^{vector}$ cells were applied to each well (1.5×$10^6$/0.15 ml in CM). After a 25 minute incubation at RT on a rotating shaker at 50 rpm, the tops of the wells were removed and the slides washed 3×in DMEM and then fixed by incubation in 1.5% glutaraldehyde (Kodak)/DMEM. Three to six 100×fields were counted for each data point and the average and standard error are reported. Data reported are from representative experiments which were performed 2–5 times with similar results.

Inhibition of Binding of ELAM-1 Containing Cells by Compounds

One hundred and twenty nanograms of Sialyl $Le^a$-HSA or Sialyl $Le^x$-HSA dissolved in 100 μl of phosphate-buffered saline were absorbed per well of an 8 chambered glass (LabTek) slide for 2 hours at room temperature. During this period, L1-$2^{ELAM-1}$ cells were pre-incubated for 20 minutes on ice with increasing concentrations of Sialyl $Le^a$-HSA at $10^7$ cells/ml. After washing and blocking the wells in Complete Medium (CM, 5% normal bovine serum, 10 mM HEPES, pH 7.0, DMEM), L1-$2^{ELAM-1}$ cells pre-incubated with compounds were added (1×$10^7$ cells/ml) and incubated at room temperature while rotating at 50 rpm. After 25 minutes, slides were washed 3 times in Dulbecco's Modified Eagles Medium (DMEM) and then fixed in 1.5% glutaraldehyde/DMEM.

Inhibition of Intercellular Adhesion by Compounds

Normal human neutrophils or peripheral blood mononuclear cells (PBMC) (1–2×$10^6$/ml) are incubated in CM for 30 minutes at room temperature while rotating at 50 rpm on a layer of COS cells transfected with ELAM-1 cDNA. After washing, the binding of neutrophils is determined by directly counting the number of neutrophils bound per transfected COS cell. For PBMC, non-adherent cells are removed by washing with DMEM and then adherent cells are removed by washing with a solution of 5 mM EDTA, 5 mM EGTA in PBS. Binding of monocytes is assessed by determining the fraction of adherent and non-adherent monocytes by FACS analysis and the number of CLA$^+$ lymphocytes by staining with the anti-CLA mAb HECA-452 [Picker, et al. (1991) *Nature* 349, 796–799]. Neutrophils and/or PBMC are pre-incubated with Sialyl-$Le^a$-HSA or other compounds prior to incubation on the layer of ELAM-1 CDNA transfected COS cells. Inhibition of intercellular adhesion is determined as a percentage calculated by:

$$\frac{\text{number of bound cells in control} - \text{number of bound cells in test}}{\text{number of bound cells in control}} \times 100$$

Binding of Lymphocytes of LECAM-1 CDNA Transfectants to High Endothelial Venules The interaction of the peripheral lymph node homing receptors (LECAM-1) with high endothelial venules is measured in a frozen section assay in which a suspension of lymphocytes and/or LECAM-1 transfected cell lines are incubated on frozen sections of lymphoid tissues for 20–30 minutes at 7° C. [Stamper and Woodruff (1976) *J. of Exp. Med.* 144, 828; Butcher, et al., (1980) *Eur. J. Immunol.* 10, 556]. After glutaraldehyde fixation, the number of cells bound per HEV is determined microscopically. Sialyl-Le$^a$-HSA and other compounds are pre-incubated with lymphocytes or transfected cell lines, including LECAM-1 and ELAM-1 transfected L1-2 cells, prior to the assay, and the ability of the compounds to inhibit intercellular adhesion is determined as described above.

Hard Sphere Exo-Anomeric (HSEA) Calculations

Conformational models of the oligosaccharides in solution were obtained by HSEA calculations. Hydroxyl groups are represented by the oxygen atoms. A fixed bond angle of 117° was used for the glycosidic linkages. The energy calculated by an HSEA potential (Bock (1983) *Pure Appl. Chem.* 55:605–622), was minimized using simultaneous variation of dihedral angles (multi-dimensional binary chop). This algorithm shows a slow convergence near a local minimum when compared to other methods utilizing the first and second derivative, but has the advantage of allowing a large initial search area of the conformational space, whereby the chances of finding the lowest local minima increases. Other applications of this program are described in Kumlien et al. (1989) *Arch. Biochem. Biophys.* 269:678–689 and Wreslander et al. (1990) *Glycoconjugate J.* 7:85–100.

Results and Discussion

Carbohydrate Epitope of Antibody HECA-452

Antibody HECA-452 was tested for direct binding to a wide variety of carbohydrate structures by assaying a panel of neoglycoproteins which were produced by chemically coupling specific oligosaccharides to serum albumin. HECA-452 binds both Sialyl Le$^a$ and Sialyl Le$^x$ hexasaccharides but not a large variety of other similar but not identical carbohydrate sequences. In comparison, antibody CSLEX-1 which has been reported to bind Sialyl Le$^x$ (Fukushima et al. (1984) *Cancer Res.* 44:5279–86) recognizes an epitope specific to Sialyl Le$^x$ and not present in Sialyl Le$^a$. Likewise, antibody 1H10, binds to Sialyl Le$^a$ but not Sialyl Le$^x$. 1H10 also weakly crossreacts with LSTa which is defucosylated Sialyl Le$^a$. Titration of the antigens further demonstrates that HECA-452 binds both Sialyl Le$^a$ and Sialyl Le$^x$ hexasaccharides with similar relative affinities whereas CSLEX-1 and 1H10 maintain specificity to either Sialyl Le$^x$ or Sialyl Le$^a$ hexasaccharide, respectively.

Carbohydrate Structure Recognized by ELAM-1

The LEC-CAM gene family consists of three membrane bound glycoproteins, ELAM-1, LECAM-1 and GMP-140 (PADGEM, CD62), which have similar domain structures featuring a mammalian C-type lectin domain at their N termini. Several studies confirm that the calcium dependent lectin domains of these molecules are of central importance to their adhesive functions. More recently, the Sialyl Le$^x$ antigen has been shown to be a neutrophil ligand for ELAM-1 (Lowe et al. (1990) *Cell* 63:475–484; Phillips et al. (1990) *Science* 250:1130–32; and Walz et al. (1990) *Science* 250:1132–35), and sialic acid moieties perhaps associated with Le$^x$ on neutrophils are thought to be important for GMP-140 binding (Larsen et al. (1989) *Cell* 59:305–12; Moore et al. (1991) *J. Cell Biol.* 112:491–99; Corral et al. (1990) *Biophys. Biochem. Res. Comm.* 172:1346–49).

ELAM-1 appears to bind structures other than Sialyl Le$^x$. A population of skin-homing memory T lymphocytes, characterized by their expression of a carbohydrate antigen, the cutaneous lymphocyte-associated antigen (CLA) defined by antibody HECA-452, were found to interact specifically with ELAM-1 even though lymphocytes do not express significant levels of Sialyl Le$^x$. Furthermore, when isolated from various sources, glycoproteins recognized by the anti-CLA mAb, HECA-452, are adhesive for ELAM-1 cDNA transfectants. Indeed, the association between expression of the HECA-452 epitope and the ability to bind ELAM-1 appeared to be quite close and suggested that ELAM-1 and HECA-452 recognize very similar carbohydrate structures. A sensitive binding assay was developed using cells permanently transfected with ELAM-1 cDNA. The mouse pre-B cell line, L1-2, transfected with ELAM-1 cDNA (L1-2$^{ELAM-1}$), but not vector control cDNA, L1-2$^{vector}$ expresses very high levels of ELAM-1. The ELAM-1 expressed by these cells is functional as L1-2$^{ELAM-1}$ cells are adhesive for neutrophils and this adhesion is blocked by anti-ELAM-1 monoclonal antibodies. When added to glass slides coated with various synthetic glycoconjugates, L1-2$^{ELAM-1}$ cells bound selectively to Sialyl Le$^a$ and Sialyl Le$^x$ neoglycoproteins, but not to a number of other glycoconjugates, (see Table I for structures). L1-2$^{ELAM-1}$ cells also bound, albeit more weakly, to Le$^a$ neoglycoprotein. The binding to Le$^a$ is significant as L1-2$^{ELAM-1}$ cells bound poorly to Le$^x$ and not at all to the glycoconjugates prepared with the structural analogs such as LNF I. That L1-2$^{ELAM-1}$ cells did not bind other monosialylated carbohydrates, such as 3'SL, 6'SL, LSTa or LSTc demonstrates that the binding to Sialyl Le$^a$ and Sialyl Le$^x$ is not due to non-specific charge effects, but rather reflects specific structural features of these oligosaccharides. The results confirm that ELAM-1 and HECA-452 recognize a very similar oligosaccharide domain, presented by both the Sialyl Le$^a$ and Sialyl Le$^x$ antigens. As shown in Table I, these hexasaccharides have the same sugar composition, but differ sterochemically in that the galactose and the fucose residues are attached to GlcNAc in the 4 and 3 positions respectively in Sialyl Le$^x$ (type 2 chain), and in the reverse positions in Sialyl Le$^a$ (type 1 chain). The low level of binding of ELAM-1 transfectants to Le$^a$ is consistent with an essential role of fucose in recognition but argues that neuraminic acid also plays a key role.

Carbohydrate Structures that Inhibit the Binding of ELAM-1 Dependent Intercellular Adhesion Sialyl Le$^a$-HSA in solution blocks 100% of binding of ELAM-1 transfected cells (L1-2$^{ELAM-1}$) to either immobilized Sialyl Le$^x$-HSA or immobilized Sialyl Le$^a$-HSA. As binding to either carbohydrate structure is blocked by Sialyl Le$^a$-HSA, only one carbohydrate-binding site exists in ELAM-1 which recognizes a carbohydrate domain common to both Sialyl Le$^a$ and Sialyl Le$^x$.

Graphic Representation of the Carbohydrate Epitope for ELAM-1.

The dihedral angles for Sialyl Le$^a$ and Sialyl Le$^x$ hexasaccharide determined by the HSEA calculations are presented in Table 2. It should be noted that these are theoretical approximations of the native conformation and the disclosure is not restricted to these bond angles. The dihedral angles are specified by the designation of the four atoms defining it. These 4-character designations are made up of the chemical symbol, 2 characters for the number in the monosaccharide (and possible extra specification e.g. to distinguish atoms of the same type bonded to the same carbon), and number of the monosaccharide residue in the oligosaccharide. The last number is defined below:

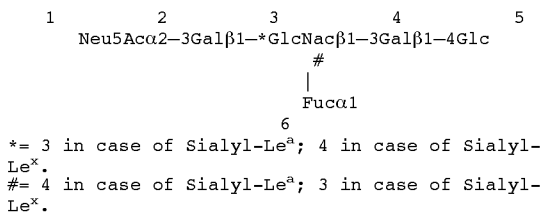

\* = 3 in case of Sialyl-Le$^a$; 4 in case of Sialyl-Le$^x$.
\# = 4 in case of Sialyl-Le$^a$; 3 in case of Sialyl-Le$^x$.

TABLE 2

| Dihedral Angle | Sialyl-Le$^a$ (°) | Sialyl-Le$^x$ (°) |
| --- | --- | --- |
| C1 1 - C2 1 - 02 1 - C3 2 | 188.6240387 | 189.0001221 |
| C2 1 - 02 1 - C3 2 - H3 2 | 350.8763428 | 349.9999695 |
| H1 2 - C1 2 - 01 2 - C* 3 | 51.3739777 | 53.2507896 |
| C1 2 - 01 2 - C* 3 - H* 3 | 15.3727636 | 8.8746433 |
| H1 3 - C1 3 - 01 3 - C3 4 | 57.8722878 | 57.8755035 |
| C1 3 - 01 3 - C3 4 - H3 4 | 350.6306458 | 350.6243591 |
| H1 4 - C1 4 - 01 4 - C4 5 | 55.3822517 | 55.4999657 |
| C1 4 - 01 4 - C4 5 - H4 5 | 2.6262217 | 1.6283444 |
| H1 6 - C1 6 - 01 6 - C# 3 | 49.7558937 | 49.8749161 |
| C1 6 - 01 6 - C# 3 - H# 3 | 18.8635368 | 23.9994240 |
| 09 1 - C9 1 - C8 1 - C7 1 | 178.1011200 | 178.2247772 |
| 08 1 - C8 1 - C7 1 - C6 1 | 299.6979065 | 300.0729675 |
| 07 1 - C7 1 - C6 1 - H6 1 | 180.4196625 | 182.0449371 |
| 06 2 - C6 2 - C5 2 - H5 2 | 303.0703125 | 300.8233032 |
| 06 3 - C6 3 - C5 3 - H5 3 | 289.2540588 | 294.3686523 |
| 06 4 - C6 4 - C5 4 - H5 4 | 306.4527283 | 306.4491882 |
| 06 5 - C6 5 - C5 5 - H5 5 | 296.1771851 | 178.0553131 |
| H6A6 - C6 6 - C5 6 - H5 6 | 179.6257324 | 179.8791046 |

\* = 3 in case of Sialyl-Le$^a$; 4 in case of Sialyl-Le$^x$.
\# = 4 in case of Sialyl-Le$^a$; 3 in case of Sialyl-Le$^x$.

EMIN (Sialyl-Le$^a$)=−15.7628746 kcal/mol
EMIN (Sialyl-Le$^x$)=−14.9528790 kcal/mol For control purposes the full program output is presented, while the relevant accuracy for comparison with experimental data cannot be expected to be higher than ± for the angles. The error in the HSEA energy value can be expected to lie in the first decimal, when given in kcal/mol. These energy values are of interest when comparing different potential functions etc., but does not lend itself easily to comparison with energies determined from experiments. A large negative value does however show that the attractive van der Waals forces dominate the calculations, giving support for the use of the HSEA approximation (positive energies indicate strong steric forces that may distort bond lengths and angles, which are assumed constant in HSEA). The resulting structures are represented graphically in FIG. 1.

The calculations show high similarity in the corresponding dihedral angles for the two structures, also at the bonds with different linkage between the N-acetyl-glucosamine and the fucose and sialic acid residues, respectively. The different dihedral angles for the hydroxymethyl group in the 6-position of the glucose residue at the reducing terminal (296.2° and 178.1°) is a result of the very nearly equal energies for this molecular group after a rotation of 120°. As this group is far away from the linkages differing between Sialyl Le$^a$ and Sialyl Le$^x$, its direction is of no importance for the conformational structure in this region. Computer-generated stereo images of the structures are represented graphically in FIG. 1. The conformations indicate that the structures show a high degree of similarity in both the non-reducing and reducing terminal parts, respectively. In particular, the structures of the terminal carbohydrate sequence up to but not including the N-acetyl group on the internal GlcNAc residue, show a high degree of homology and may represent the domain recognized by both ELAM-1 and the monoclonal antibody HECA-452. This area of structural homology is particularly useful for the design of potential anti-inflammatory drugs.

Examples of other carbohydrate-binding proteins that recognize type 1 and type 2 chain isomers are the antibodies E$_1$23-48 and E$_1$66-18 which bind the blood group B antigen (Hansson et al. (1983) *J. Biol. Chem.* 258:4091–97) and the lectin, *Griffonia simplicifolia IV*, which recognizes both Le$^b$ and Le$^y$ antigens (Spohr et al. (1985) *Can. J. Chem.* 63:2644–52).

The recognition of the Sialyl Le$^a$ antigen and the Sialyl Le$^x$ antigen, by ELAM-1, may be of pathologic importance. Mucins containing this structure are elevated in the sera of cancer patients, including gastrointestinal, pancreatic, and breast cancer patients (Magnani et al. (1982) *J. Biol. Chem.* 257:14365–369; Magnani et al. (1983) *Cancer Res.* 43:5481–92). Preliminary experiments indicate that some Sialyl Le$^a$ and Sialyl Le$^x$-containing mucins are recognized by ELAM-1 transfectants. By interacting with ELAM-1 on venules in acute and chronically inflamed tissues and interfering with the recruitment of leukocytes to these locations, these mucins secreted by tumors may contribute to the immunodepressed state of cancer patients.

It is evident from the above results, that compositions can be employed which can be used to modulate the homing of leukocytes, particularly lymphocytes, to sites of inflammation. These compounds can be readily prepared by conventional ways and can be effective for the treatment of a variety of diseases, both prophylactically and therapeutically.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for modulating the binding of leukocytes to endothelial cells expressing ELAM-1, said method comprising:

adding to a combination of cells comprising leukocytes and endothelial cells expressing ELAM-1, in an amount sufficient to modulate the binding of leukocytes to said ELAM-1, a glycoconjugate of sialyl-Le$^a$ or derivative thereof.

2. A method for inhibiting infiltration of leukocytes into an inflammation site of a host, said method comprising:

administering to said host in an amount sufficient to inhibit leukocyte infiltration, a glycoconjugate of sialyl-Le$^a$ or derivative thereof.

3. A method for inhibiting infiltration of lymphocytes into an inflammation site of a host, said method comprising:

administering to said host in an amount sufficient to inhibit lymphocyte infiltration, a glycoconjugate of sialyl-Le$^a$ or derivative thereof.

\* \* \* \* \*

UNITED STATES PATENT AND TRADEMARK OFFICE
CERTIFICATE OF CORRECTION

| | | |
|---|---|---|
| PATENT NO. | : 6,387,884 B1 | |
| APPLICATION NO. | : 08/336417 | |
| DATED | : May 14, 2002 | |
| INVENTOR(S) | : Magnani et al. | |

It is certified that error appears in the above-identified patent and that said Letters Patent is hereby corrected as shown below:

In The Specification Under Column 1:

Insert at line 4:

-- FEDERALLY-SPONSORED RESEARCH OR DEVELOPMENT
This invention was made with Government support under contract GM037734 awarded by the National Institutes of Health. The Government has certain rights in this invention. --

Signed and Sealed this
Thirty-first Day of January, 2012

David J. Kappos
*Director of the United States Patent and Trademark Office*